US008338353B2

(12) United States Patent
Martyak et al.

(10) Patent No.: US 8,338,353 B2
(45) Date of Patent: Dec. 25, 2012

(54) HARD SURFACE CLEANER CONTAINING POLYSULFONIC ACID

(75) Inventors: Nicholas M. Martyak, Doylestown, PA (US); Gary E. Stringer, Birdsboro, PA (US)

(73) Assignee: Arkema Inc., King of Prussia, PA (US)

( * ) Notice: Subject to any disclaimer, the term of this patent is extended or adjusted under 35 U.S.C. 154(b) by 280 days.

(21) Appl. No.: 12/667,589

(22) PCT Filed: Jul. 24, 2008

(86) PCT No.: PCT/US2008/070966
§ 371 (c)(1),
(2), (4) Date: Jan. 4, 2010

(87) PCT Pub. No.: WO2009/020767
PCT Pub. Date: Feb. 12, 2009

(65) Prior Publication Data
US 2011/0015112 A1    Jan. 20, 2011

Related U.S. Application Data

(60) Provisional application No. 60/954,334, filed on Aug. 7, 2007.

(51) Int. Cl.
*C11D 1/12*    (2006.01)
*C11D 1/83*    (2006.01)

(52) U.S. Cl. ........ 510/238; 510/253; 510/260; 510/362; 510/421; 510/422; 510/426; 510/427

(58) Field of Classification Search ............... 510/238, 510/253, 260, 362, 421, 422, 426, 427
See application file for complete search history.

(56) References Cited

U.S. PATENT DOCUMENTS

| | | | | |
|---|---|---|---|---|
| 3,943,234 A * | 3/1976 | Roggenkamp | ............... | 514/724 |
| 4,215,000 A * | 7/1980 | De Jong et al. | ............... | 507/241 |
| 4,421,611 A * | 12/1983 | Cameron | .................. | 205/275 |
| 4,588,481 A * | 5/1986 | Chessin et al. | ............... | 205/290 |
| 4,673,523 A * | 6/1987 | Smith et al. | ............... | 15/104.93 |
| 4,704,222 A * | 11/1987 | Smith | ..................... | 510/396 |
| H0000404 H * | 1/1988 | Sayles | ..................... | 405/129.25 |
| 4,917,814 A * | 4/1990 | MacIntyre et al. | ........... | 510/373 |
| 4,975,274 A * | 12/1990 | Iannucci et al. | ............. | 424/70.1 |
| 5,604,195 A * | 2/1997 | Misselyn et al. | ............. | 510/400 |
| 5,733,342 A * | 3/1998 | Greindl et al. | .................. | 8/137 |
| 5,977,054 A * | 11/1999 | Wierenga | ..................... | 510/503 |
| 6,179,880 B1 * | 1/2001 | Smith | ............... | 8/142 |
| 6,217,855 B1 * | 4/2001 | Itou et al. | ..................... | 424/70.2 |
| 2003/0199406 A1 * | 10/2003 | Anzures et al. | ............. | 510/175 |
| 2004/0266644 A1 | 12/2004 | Seebach et al. | | |
| 2007/0059380 A1 | 3/2007 | Ramirez et al. | | |
| 2008/0236619 A1 * | 10/2008 | Chen et al. | ...................... | 134/3 |

* cited by examiner

*Primary Examiner* — Charles Boyer
(74) *Attorney, Agent, or Firm* — Steven D. Boyd

(57) ABSTRACT

The invention is directed toward improved aqueous hard surface cleaning compositions which include one or more polysulfonic acids The inclusion of one or more polysulfonic acids in a hard surface composition provides for improved removal of insoluble salt deposits resulting from hard water In an embodiment, the invention utilizes a foaming agent fragrance and a thickening agent.

10 Claims, No Drawings

HARD SURFACE CLEANER CONTAINING POLYSULFONIC ACID

FIELD OF THE INVENTION

This present invention relates to improved cleaners for hard surfaces. More particularly the present invention relates to improved hard surface cleaners for use in applications such as kitchens, bathrooms and others, where the improvement entails the addition of polysulfonic acid to a cleaner formulation.

BACKGROUND OF THE INVENTION

The present invention relates to improved cleaning compositions which find particular use in hard surface cleaning applications. Hard surface cleaning compositions have been known and used in a variety of applications, including bathrooms, kitchens and other areas, particularly for toilets, showers, bathtubs, sinks, tiles, countertops, walls, floors and the like. Often times, hard surfaces accumulate both soap scum stains, which are typically residues of various types of soaps used in a household, as well as hard water stains, which are typically the result of the deposition of calcium, barium and lime or various salts on hard surfaces over the course of time and use of various household surfaces.

Cleaning solutions for these household surfaces have been formulated to address both the removal of soap scum stains, as well as the descaling of hard water stains. In particular, many of these cleaning solutions have employed a combination of components, in a number of instances including strong inorganic acids, organic acids or a combination of both, a surfactant or wetting agent, a solvent and a diluent to address one or both of these types of stains and/or build-ups. The acid component is typically selected to address descaling of hard water stains, while the surfactant component is typically a detergent selected to attack soap scum. For example, it is known to the art that highly acidic cleaning agents comprising strong acids, such as hydrochloric acids, are useful in the removal of hard water stains. Further, other additives have also been used in combination with cleaning formulations to either enhance performance or make a particular formulation more desirable from a visual or odor perspective, such as pH adjusters, stabilizing agents, colorants and fragrances, amongst others. U.S. Pat. Nos. 4,923,523 and 4,975,216 disclose the use of short-chain alkane sulfonic acids such as methane sulfonic acid in cleaning and/or disinfecting compositions.

SUMMARY OF THE INVENTION

Thus, it is among the objects of the invention to provide improved cleaning compositions which provides the benefit of hard water stain removal, especially from hard surfaces. It is a further object of the invention to provide improved cleaning compositions which are particularly effective in hard water stain removal, and which further features minimal irritability to the eyes, skin or mucous tissues of a consumer.

It is a further object of the invention to provide a process for the improvement of the cleaning of hard surfaces, which process comprises the step of: providing a cleaning composition including one or more polysulfonic acids, and applying an effective amount to a hard surface requiring such treatment.

These and other objects of the invention shall be more apparent from a reading of the following specification and of the claims.

According to the invention, there is provided an improved aqueous hard surface cleaning compositions. The compositions include one or more polysulfonic acids.

The compositions of the invention may also include one or more further optional constituents such as known art additives. By way of non-limiting example, such constituents include: further surfactants, particularly surfactants which are useful for the removal of greasy soils, foaming agents and foam stabilizers, coloring agents, including dyes and pigment compositions, fragrances (whether natural or synthetically produced), fragrance adjuvants and/or fragrance solubilizers, viscosity modifying agents including thickeners or gelling agents, pH-adjusting agents, pH buffers, antioxidants, water softening agents, further solubilizing agents which might be useful in the solubilization of one or more of the constituents in water, preservative compositions, as well as other known art additives not particularly elucidated here.

The compositions according to the invention are preferably acidic in character, exhibiting a pH of less than 7. Desirably, the pH is in the range of about 1 to about 5, yet more desirably is a pH in the range of about 1 to about 4, and most desirably is a pH of about 1 to about 3.

DESCRIPTION OF THE INVENTION

The present invention is directed to improved liquid cleaning solutions which are particularly suited for removing hard water stains, lime scale and the like from various hard surfaces such as tubs, tiles, showers, sinks and other areas which are exposed to water and soap. The invention includes different embodiments, including cleaning solutions suitable for removing hard water stains, lime scale and rust, which incorporate one or more polysulfonic acids. The one or more polysulfonic acids of the present invention include, but are not limited to alkyl and/or aryl polysulfonic acids such as methanedisulfonic acid, ethanedisulfonic acid, propanedisulfonic acid and 1,3,6 naphthalene trisulfonic acid among other.

The compositions according to the present invention may comprise one or more of the following optional components, the total weight of such optional constituents preferably not exceeding about 20% by weight of the total weight of the composition, more preferably not exceeding about 10% by weight, and most preferably less than 10% by weight based on the total weight of the composition according to the invention.

Non-ionic surfactants of the conventionally known and used variety in this class of cleaning agents may be added in effective amounts, i.e., amounts which are shown to be effective in the cleaning compositions in facilitating the removal of greasy soils. Such greasy soils are to be differentiated from the hard water stains described earlier in this specification. Exemplary nonionic surfactants include known nonionic surfactants which generally consist of a hydrophobic moiety, such as $C_6$-$C_{20}$ primary or secondary, branched or straight chain monoalcohols, $C_8$-$C_{18}$ mono- or dialkyphenols, $C_6$-$C_{20}$ fatty acid amides, and a hydrophilic moiety which consists of alkylene oxide units. These nonionic surfactants are, for instance, alkoxylation products of the above hydrophobic moieties, containing from 2 to 30 moles of alkylene oxide. As alkylene oxides, ethylene-, propylene- and butylene oxides and mixtures thereof are used.

Typical examples of such nonionic surfactants are $C_9$-$C_{11}$ primary, straight-chain alcohols condensed with 5-9 moles of ethylene oxide, $C_{12}$-$C_{15}$ primary straight chain alcohols condensed with from 6-12 moles of ethylene oxide, or with 7-9 moles of a mixture of ethylene oxide and propylene oxide, $C_{11}$-$C_{15}$ secondary alcohols condensed with from 3-15 moles of ethylene oxide, and $C_{10}$-$C_{18}$ fatty acid diethanolamides, and tertiary amine oxides such as higher alkyl di(lower alkyl or lower substituted alkyl)amine oxides. Other useful nonionic surfactants include certain alkoxylated linear aliphatic alcohol surfactants which are believed to be the condensation products of a $C_8$-$C_{10}$ hydrophilic moiety with alkylene oxides, especially polyethylene oxide and or polypropylene oxide moieties. Such nonionic surfactants are known to the art, and are more particularly described in McCutcheon's Detergents and Emulsifiers, noted above.

Foaming agents, and foam stabilizing agents may be provided, including alkyl sulfates, alkyl sulfonates, amine oxides, as well as alkanolamides. Such may be especially desirable where the composition is packaged in a pressurized device, i.e., an aerosol canister or in a hand-held pumpable container (such as a hand held trigger-spraying vessel).

Further optional, but desirable constituents, include fragrances, natural or synthetically produced. Such fragrances may be added in any conventional manner, admixing to a composition or blending with other constituents used to form a composition, in amounts which are found to be useful to enhance or impart the desired scent characteristic to the composition, and/or to cleaning compositions formed there from.

In compositions which include a fragrance, it is frequently desirable to include a fragrance solubilizer which assists in the dispersion, solution or mixing of the fragrance constituent in an aqueous base. These include known art compounds, including condensates of 2 to 30 moles of ethylene oxide with sorbitan mono- and tri-$C_{10}$-$C_{20}$ alkanoic acid esters having a HLB of 8 to 17 are also known as nonionic surfactants. Further examples of such suitable surfactants include water soluble nonionic surfactants of which many are commercially known and, by way of non-limiting example, include the primary aliphatic alcohol ethoxylates, secondary aliphatic alcohol ethoxylates, alkylphenol ethoxylates and ethyleneoxide-propylene oxide condensates of primary alkanols, and condensates of ethylene oxide with sorbitan fatty acid esters. This fragrance solubilizer component is added in minor amounts, preferably in an amount effective in aiding in the solubilization of the fragrance component, but not in any significantly greater proportion, such that it would be considered as a detergent constituent. Such minor amounts recited herein are generally up to about 0.5% by weight of the total composition, but more generally present an amount of about 0.1% by weight and less, and preferably present in amounts of about 0.05% by weight and less.

Further optional, but advantageously included constituents are one or more coloring agents which find use in modifying the appearance of the compositions and enhance their appearance from the perspective of a consumer or other end user. Known coloring agents may be incorporated in the compositions in any effective amount to improve or impart to compositions a desired appearance or color. Such a coloring agent or coloring agents may be added in a conventional fashion, i.e., admixing to a composition or blending with other constituents used to form a composition.

The use of one or more pH-adjusting agents, including minor amounts of mineral acids, basic compositions, and organic acids may be used. An exemplary composition includes citric acid, such as is available in an anhydrous salt form of an alkali metal citric acid. The addition of an effective amount of such a pH-adjusting agent is useful in establishing a targeted pH range for compositions according to the invention. The addition of an effective amount of a pH buffering composition so as to maintain the pH of the inventive compositions may also be added. While the composition of the invention generally does not require a pH buffering composition, the use of such a pH buffering composition may provide the benefit of hard water ion sequestration. Examples of such useful pH buffer compounds and/or pH buffering systems or compositions are alkali metal phosphates, polyphosphates, phosphonates, pyrophosphates, triphosphates, tetraphosphates, silicates, metasilicates, polysilicates, carbonates, hydroxides, and mixtures of the same. Certain salts, such as the alkaline earth phosphates, carbonates, hydroxides, can also function as buffers. It may also be suitable to use as buffers such materials as aluminosilicates (zeolites), borates, aluminates and certain organic materials such as gluconates, succinates, maleates, citrates, and their alkali metal salts. Such buffers keep the pH ranges of the compositions of the present invention within acceptable limits. Others, not particularly elucidated here may also be used. Preferably, citric acid, such as is available in an anhydrous salt form of an alkali metal citric acid is added as it is readily commercially available, and effective. The addition of such a buffering agent is desirable in certain cases wherein long term, i.e., prolonged storage, is to be anticipated for a composition, as well as insuring the safe handling of said aqueous composition.

Preservatives which do not include a disinfectant component may also be added in minor amounts in the formulations according to the invention. Compositions known in the art may be used. Examples of such preservatives compounds include those which are presently commercially available under the trademarks Kathon®. CG/ICP (Rohm & Haas, Philadelphia Pa.), Suttocide® A (Sutton Labs, Chatham N.J.) as well as Midtect® TFP (Tri-K Co., Emerson, N.J.). Such preservatives are generally added in only minor amounts, i.e., amounts of about 0.5% by weight of the total composition, more generally an amount of about 0.1% by weight and less, and preferably present in amounts of about 0.05% by weight and less.

Thickening and/or gelling agents may be added to the hard surface cleaning compositions according to the present invention in order to modify the viscous and/or thixatropic properties thereof. For example, in certain applications it is contemplated that it may be desirable to provide a more viscous, higher viscosity than that of water, whether for aesthetic or functional reasons.

For example, the addition of a suitable amount of a gelling agent may be desired not only for aesthetic reasons but also to limit the spreading of the composition as it is applied to a surface. This function is desirable in providing a means to apply the composition over a limited area, such as directly onto a stain, without applying an excess onto the surrounding area of a surface. This function also aids in the surface retention time on non-horizontal surfaces, ensuring that the cleaning composition is in contact with a stained surface without flowing off too rapidly. Similarly, thixotropic properties may also be desired under certain circumstances. In order to provide such functional features to the composition, known thickening and gelling agents including, but not limited to, cellulose compounds, xanthan gums, polymers and/or clays may be added. For xanthan gums, those available under the Kelco or Keltrol trademarks are useful.

The compositions according to the invention are useful in the cleaning of hard surfaces, having deposited soil thereon. In such a process, cleaning of such surfaces comprises the step of applying a stain releasing effective amount of a composition as taught herein to such a stained surface. Afterwards, the compositions are optionally but desirably wiped, scrubbed or otherwise physically contacted with the hard surface, and further optionally, may be subsequently rinsed from such a cleaned hard surface.

The hard surface cleaner composition provided according to the invention can be desirably provided as a ready to use product in a manually operated spray-dispensing container. Such a typical container is generally made of synthetic polymer plastic material, such as polyethylene, polypropylene, polyvinyl chloride or the like, and includes a spray nozzle, a dip tube and associated pump dispensing parts, and is thus ideally suited for use in a consumer "spray and wipe" application. In such an application, the consumer generally applies an effective amount of the cleaning composition using the pump and within a few moments thereafter, wipes off the treated area with a rag, towel, or sponge, usually a disposable paper towel or sponge. In certain applications, however, especially where undesirable stain deposits are heavy, the cleaning composition according to the invention may be left on the stained area until it has effectively loosened the stain deposits, after which it may then be wiped off, rinsed off, or otherwise removed. For particularly heavy deposits of such undesired stains, multiple applications may also be used.

In a yet a further embodiment, the compositions according to the invention may be formulated so that they may be useful in conjunction with an "aerosol" type product wherein they are discharged from a pressurized aerosol container. If the inventive compositions are used in an aerosol type product, it is preferred that corrosion resistant aerosol containers, such as coated or lined aerosol containers be used. Such are preferred, as they are known to be resistant to the effects of acidic formulations. Known art propellants, such as liquid propellants as well as propellants of the non-liquid form, i.e., pressurized gases, including carbon dioxide, air, nitrogen, hydrocarbons as well as others may be used.

Whereas the present invention is intended to be used in the types of liquid forms described, nothing in this specification shall be understood as to limit the use of the composition according to the invention with a further amount of water to form a cleaning solution there from. In such a proposed diluted cleaning solution, the greater the proportion of water added to form said cleaning solution, the greater may be the reduction of the rate and/or efficacy of the thus formed cleaning solution in the cleaning of a hard surface, as well as a reduction in disinfectant efficacy.

Accordingly, longer residence times upon the stain to effect their loosening and/or the usage of greater amounts may be necessitated. Conversely, nothing in the specification shall be also understood to limit the forming of a "super-concentrated" cleaning composition based upon the composition described above. Such a super-concentrated composition is essentially the same as the compositions described above except in that they include a lesser amount of water.

While the cleaning compositions are most beneficial for use in their form, i.e., their form as described above, they may also be diluted to form a cleaning composition there from. Such cleaning compositions may be easily prepared by diluting measured amounts of the compositions in further amounts of water by the consumer or other end user in certain weight ratios of composition to water, and optionally, agitating the same to ensure even distribution of the composition in the water. The aqueous compositions according to the invention may be used without further dilution, but may also be used with a further aqueous dilution, i.e., in composition to water concentrations of about 1:0 to extremely dilute dilutions such as about 1:10,000. but preferably would be used in a weight or volume ratio proportion of about 1:10 to about 1:100. Generally better results and faster removal are to be expected at lower relative dilutions of the composition and the water.

The following examples below illustrate exemplary formulations and preferred formulations of the composition according to the instant invention. It is to be understood that these examples are presented by means of illustration only and that further useful formulations falling within the scope of this invention and the claims may be readily produced by one skilled in the art and not deviate from the scope and spirit of the invention. Throughout this specification and in the accompanying claims, weight percents of any constituent are to be understood as the weight percent of the active portion of the referenced constituent, unless otherwise indicated.

EXAMPLES

Example 1

The effectiveness of materials to dissolve water insoluble calcium deposits was evaluated using marble. A 9 wt % concentration of acid in water was placed on a marble surface for ten minutes at room temperature. The marble was weighed both before and after application of the acid. The weight loss is an indication of the effectiveness of the acid at dissolving calcium from the marble. Table 1 summarizes the results of testing of methanedisulfonic acid, isethionic acid and methansulfonic acid (a non-polyfunctional acid control).

TABLE 1

| Acid Concentration | Weight Loss (%) |
| --- | --- |
| 9% methanedisulfonic acid | 22.5 |
| 9% isethionic acid | 12.6% |
| 9% methanesulfonic acid | 17% |

The data in Table 1 shows that methanedisulfonic acid is significantly more effective at dissolving calcium than isethionic acid or methanesulfonic acid.

Having described the invention, we now claim the following and their equivalents.

What is claimed is:

1. In a process for cleaning a hard surface contaminated with organic and/or inorganic contaminants comprising contacting the contaminated hard surface with an aqueous acidic cleaning and/or disinfectant composition, the improvement wherein said composition contains a cleaning quantity of a combination comprising:
    a) at least one polysulfonic acid selected from the group consisting of methanedisulfonic acid, ethanedisulfonic acid, propanedisulfonic acid and 1,3,6 naphthalene trisulfonic acid;
    b) a nonionic surfactant;
    c) a foaming agent selected from the group consisting of alkyl sulfates, alkyl sulfonates, amine oxides and alkanolamides wherein the foaming agent is different from the nonionic surfactant; and
    d) a fragrance, wherein said aqueous acidic cleaning and/or disinfecting composition has a pH of less than about 7.

2. The process of claim 1 wherein said at least one polysulfonic acid is present in said aqueous acidic cleaning and/or disinfecting composition in an amount of less than about 20% by weight.

3. The process of claim 1 wherein said aqueous acidic cleaning and/or disinfecting composition has a pH of from about 1 to 5.

4. The process of claim 1 wherein said aqueous acidic cleaning and/or disinfecting composition has a pH of from about 1 to 7.

5. The process of claim 1 wherein said aqueous acidic cleaning and/or disinfecting composition further comprises a thickening agent.

6. An aqueous acidic cleaning and/or disinfectant composition for hard surfaces, the improvement wherein said composition contains a cleaning quantity of:
   a) at least one polysulfonic acid selected from the group consisting of methanedisulfonic acid, ethanedisulfonic acid, propanedisulfonic acid and 1,3,6 naphthalene trisulfonic acid;
   b) a nonionic surfactant;
   c) a foaming agent selected from the group consisting of alkyl sulfates, alkyl sulfonates, amine oxides and alkanolamides wherein the foaming agent is different from the nonionic surfactant; and
   d) a fragrance, wherein said aqueous acidic cleaning and/or disinfecting composition has a pH of less than about 7.

7. The composition of claim 6 wherein said at least one polysulfonic acid is present in said aqueous acidic cleaning and/or disinfecting composition in an amount of less than about 20% by weight.

8. The composition of claim 6 wherein said aqueous acidic cleaning and/or disinfecting composition has a pH of from about 1 to 5.

9. The composition of claim 6 wherein said aqueous acidic cleaning and/or disinfecting composition has a pH of from about 1 to 7.

10. The composition of claim 6 wherein said aqueous acidic cleaning and/or disinfecting composition further comprises a thickening agent.

* * * * *